United States Patent
Cao et al.

(10) Patent No.: US 10,416,324 B2
(45) Date of Patent: Sep. 17, 2019

(54) DARK NOISE COMPENSATION IN A RADIATION DETECTOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 16/170,629

(22) Filed: Oct. 25, 2018

(65) Prior Publication Data

US 2019/0064373 A1    Feb. 28, 2019

Related U.S. Application Data

(63) Continuation of application No. PCT/CN2016/103466, filed on Oct. 27, 2016.

(51) Int. Cl.
*G01T 1/24* (2006.01)
*A61B 6/03* (2006.01)
*A61B 6/00* (2006.01)

(52) U.S. Cl.
CPC .............. *G01T 1/247* (2013.01); *A61B 6/032* (2013.01); *A61B 6/4208* (2013.01)

(58) Field of Classification Search
CPC ........ A61B 6/032; A61B 6/4208; G01T 1/247
See application file for complete search history.

(56) References Cited

U.S. PATENT DOCUMENTS 10,007,009 B2 *   6/2018   Cao ......................... G01T 1/247
2011/0198508 A1   8/2011   Groh et al.

FOREIGN PATENT DOCUMENTS

| CN | 102413763 A | 4/2012 |
|---|---|---|
| CN | 103312996 A | 9/2013 |
| JP | 2003240859 A | 8/2003 |
| WO | 2016161542 A1 | 10/2016 |
| WO | 2016161544 A1 | 10/2016 |

* cited by examiner

*Primary Examiner* — David P Porta
*Assistant Examiner* — Fani Boosalis
(74) *Attorney, Agent, or Firm* — IPro, PLLC; Qian Gu; Na Xu

(57) ABSTRACT

Disclosed herein is a radiation detector, comprising: a radiation absorption layer comprising an electrode; a capacitor module electrically connected to the electrode and comprising a capacitor, wherein the capacitor module is configured to collect charge carriers from the electrode onto the capacitor; a current sourcing module in parallel to the capacitor, the current sourcing module configured to compensate for an electrical current of a dark noise in the radiation detector and comprising a current source and a modulator; wherein the current source is configured to output a first electrical current and a second electrical current; wherein the modulator is configured to control a ratio of a duration at which the current source outputs the first electrical current to a duration at which the current source outputs the second electrical current.

41 Claims, 22 Drawing Sheets

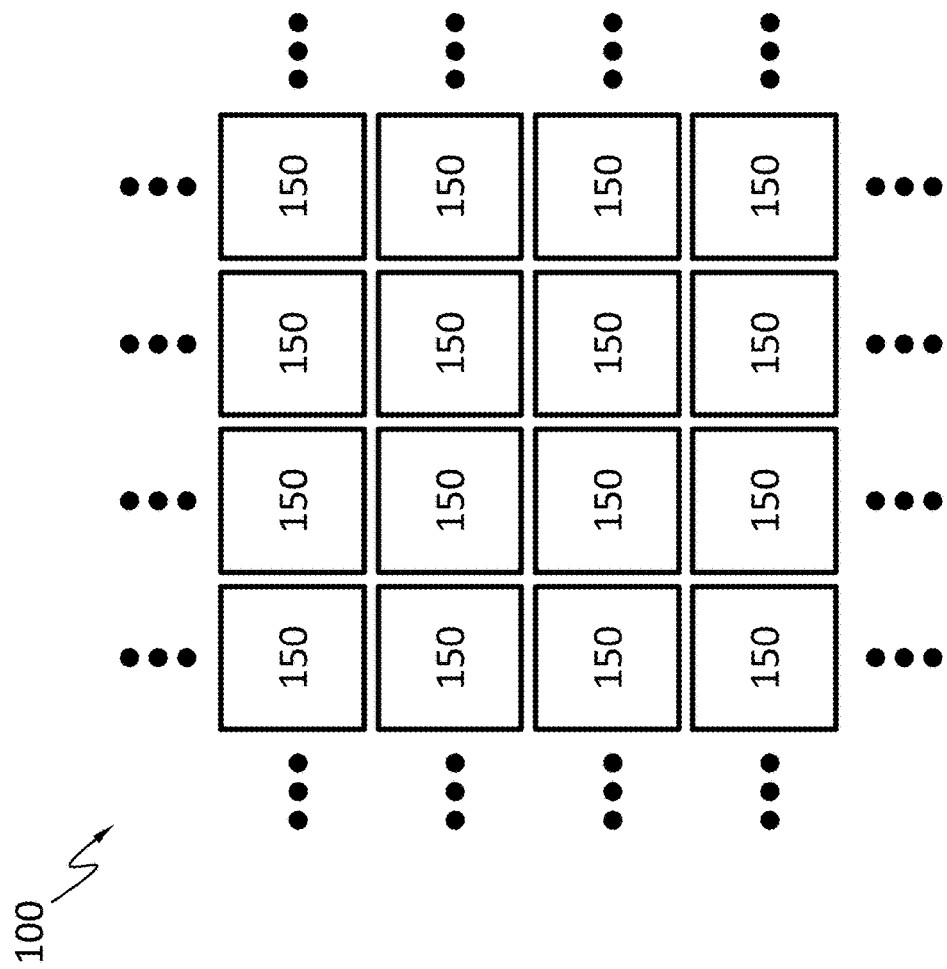

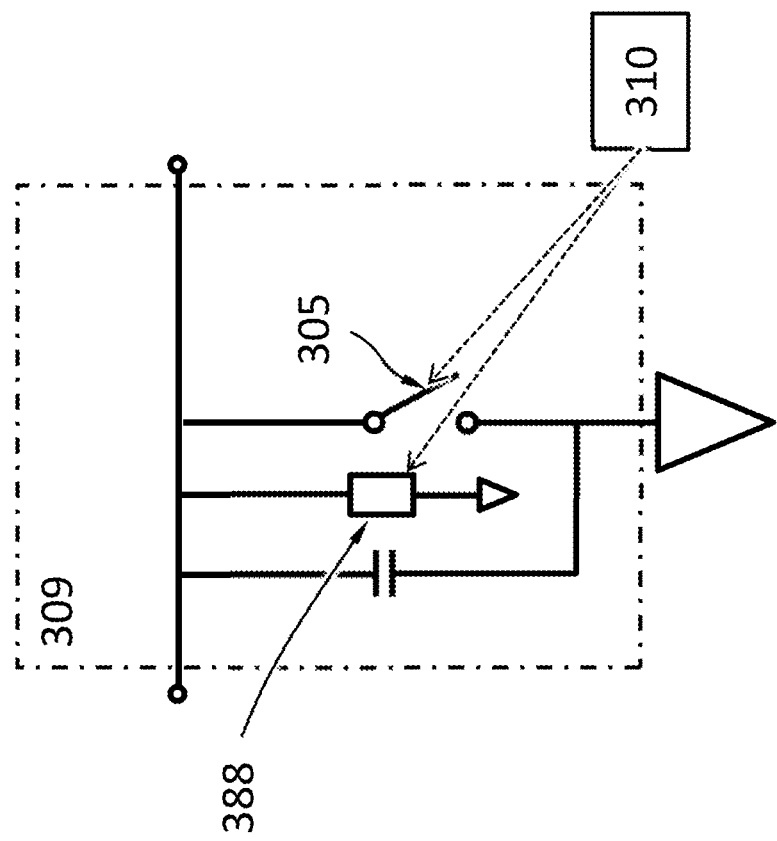

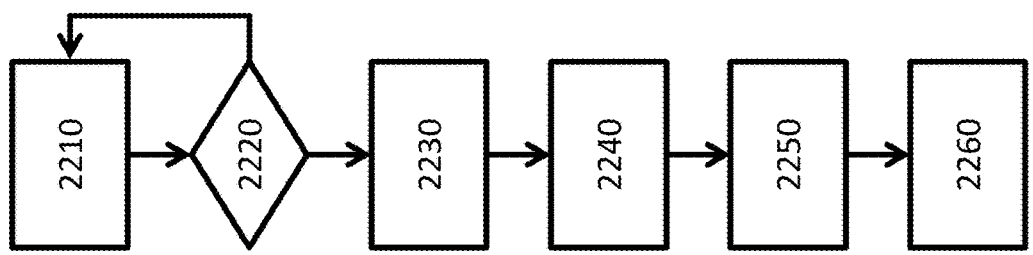

DARK NOISE COMPENSATION IN A RADIATION DETECTOR

TECHNICAL FIELD

The disclosure herein relates to methods and apparatuses for compensating for the effect of dark noise in a radiation detector such as a semiconductor X-ray detector.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays.

One type of radiation detectors is based on interaction between the radiation and a semiconductor. For example, a radiation detector of this type may have a semiconductor layer that absorbs the radiation and generate charge carriers (e.g., electrons and holes) and circuitry for detecting the charge carriers.

Radiation detectors may be negatively impacted by "dark" noise (e.g., dark current). Dark noise in a radiation detector includes physical effects present even if no radiation the radiation detector is configured to detect is incident on the radiation detector. Isolating or reducing the impact of the dark noise to the overall signals detected by the radiation detector is helpful to make the radiation detector more useful.

SUMMARY

Disclosed herein is a radiation detector, comprising: a radiation absorption layer comprising an electrode; a capacitor module electrically connected to the electrode and comprising a capacitor, wherein the capacitor module is configured to collect charge carriers from the electrode onto the capacitor; a current sourcing module in parallel to the capacitor, the current sourcing module configured to compensate for an electrical current of a dark noise in the radiation detector and comprising a current source and a modulator; wherein the current source is configured to output a first electrical current and a second electrical current; wherein the modulator is configured to control a ratio of a duration at which the current source outputs the first electrical current to a duration at which the current source outputs the second electrical current.

According to an embodiment, the current sourcing module is adjustable.

According to an embodiment, the current sourcing module is configured to divert the electrical current of the dark noise through the current sourcing module.

According to an embodiment, the first electrical current and the second electrical current are different in their magnitude, direction, or both.

According to an embodiment, least one of the first electrical current and the second electrical current is at least an order of magnitude larger than the electrical current of the dark noise.

According to an embodiment, the electrical current of the dark noise is from 1 pA to 1000 pA.

According to an embodiment, the modulator comprises a processor or a memory.

According to an embodiment, the modulator comprises a switch.

According to an embodiment, the radiation is X-ray.

According to an embodiment, the current source comprises a current mirror.

According to an embodiment, the modulator is located on an input stage of the current mirror.

According to an embodiment, the modulator comprises a current source configured to output electrical current at alternating magnitudes.

According to an embodiment, the modulator comprises a current source configured to output two magnitudes of electrical current with adjustable ratio of durations.

According to an embodiment, the modulator is located on an output stage of the current mirror.

According to an embodiment, the modulator comprises a switch configured to controllably connect the current sourcing module to and to controllably disconnect it from the capacitor.

According to an embodiment, the radiation detector further comprises: a first voltage comparator configured to compare a voltage of the electrode to a first threshold; a second voltage comparator configured to compare the voltage to a second threshold; a counter configured to register a number of X-ray photons absorbed by the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the controller is configured to activate the second voltage comparator at a beginning or expiration of the time delay.

According to an embodiment, the radiation detector further comprises a voltmeter, wherein the controller is configured to cause the voltmeter to measure the voltage upon expiration of the time delay.

According to an embodiment, the controller is configured to determine a photon energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the radiation absorption layer comprises a diode.

According to an embodiment, the radiation absorption layer comprises silicon, germanium, GaAs, CdTe, CdZnTe, or a combination thereof.

According to an embodiment, the radiation detector does not comprise a scintillator.

According to an embodiment, the radiation detector comprises an array of pixels.

Disclosed herein is a system comprising any of the above radiation detectors and an X-ray source, wherein the system is configured to perform X-ray radiography on human chest or abdomen.

Disclosed herein is a system comprising any of the above radiation detectors and an X-ray source, wherein the system is configured to perform X-ray radiography on human mouth.

Disclosed herein is a cargo scanning or non-intrusive inspection (NII) system, comprising any of the above radiation detectors and an X-ray source, wherein the cargo scanning or non-intrusive inspection (NII) system is configured to form an image using backscattered X-ray.

Disclosed herein is a cargo scanning or non-intrusive inspection (NII) system, comprising the radiation detector of any of the above radiation detectors and an X-ray source, wherein the cargo scanning or non-intrusive inspection (NII) system is configured to form an image using X-ray transmitted through an object inspected.

Disclosed herein is a full-body scanner system comprising the radiation detector of any of the above radiation detectors and a radiation source.

Disclosed herein is a computed tomography (CT) system comprising the radiation detector of any of the above radiation detectors and a radiation source.

Disclosed herein is an electron microscope comprising the radiation detector of any of the above radiation detectors, an electron source and an electronic optical system.

Disclosed herein is a system comprising the radiation detector of any of the above radiation detectors, wherein the system is an X-ray telescope, or an X-ray microscopy, or wherein the system is configured to perform mammography, industrial defect detection, microradiography, casting inspection, weld inspection, or digital subtraction angiography.

Disclosed herein is a method comprising: determining a contribution of a dark noise in signals of a radiation detector; determining a ratio of a duration of a first compensatory signal to a duration of a second compensatory signal based on the contribution of the dark noise, the first compensatory signal and the second compensatory signal; and compensating the signals of the radiation detector for the dark noise with the first compensatory signal and the second compensatory signal with their respective durations with the ratio.

According to an embodiment, the contribution is determined by measuring the signals while the radiation detector receives no radiation.

According to an embodiment, the first compensatory signal and the second compensatory signal are electrical currents.

Disclosed herein is a method comprising: measuring signals of a radiation detector when the radiation detector receives no radiation and a compensation for the dark noise of the radiation detector is present; if the signals have exceeded a first level, commencing a time delay; measuring the signals of the radiation detector at an end of the time delay; and if the signals at the end of the time delay exceed a second level, increasing the compensation for the dark noise.

According to an embodiment, the compensation is increased to a magnitude among a group of discrete values.

According to an embodiment, the method further comprises: if the signals at the end of the time delay exceed a second level, resetting the signals.

Disclosed herein is a method comprising: measuring signals of a radiation detector when the radiation detector receives no radiation and a compensation for the dark noise of the radiation detector is present; if the signals have exceeded a first level, commencing a time delay; measuring the signals of the radiation detector at an end of the time delay; determining a difference between the signals at the end of the time delay and the signals at the beginning of the time delay; and determining a magnitude of the compensation based on the difference.

BRIEF DESCRIPTION OF FIGURES

FIG. 1 schematically shows a radiation detector, according to an embodiment.

FIG. 4A and FIG. 4B respectively show a circuit configured to compensate for the dark noise in the form of an electrical current.

FIG. 11B schematically shows a flow chart for a method of compensating for dark noise in a radiation detector.

DETAILED DESCRIPTION

FIG. 1 schematically shows a radiation detector 100, as an example. The radiation detector 100 has an array of pixels 150. The array may be a rectangular array, a honeycomb array, a hexagonal array or any other suitable array. Each pixel 150 is configured to detect radiation from a radiation source incident thereon and may be configured measure a characteristic (e.g., the energy of the particles, the wavelength, and the frequency) of the radiation. For example, each pixel 150 is configured to count numbers of photons incident thereon whose energy falls in a plurality of bins, within a period of time. All the pixels 150 may be configured to count the numbers of photons incident thereon within a plurality of bins of energy within the same period of time. Each pixel 150 may have its own analog-to-digital converter (ADC) configured to digitize an analog signal representing the energy of an incident photon into a digital signal. The pixels 150 may be configured to operate in parallel. For example, when one pixel 150 measures an incident photon, another pixel 150 may be waiting for a photon to arrive. The pixels 150 may not have to be individually addressable.

Figure 2A:
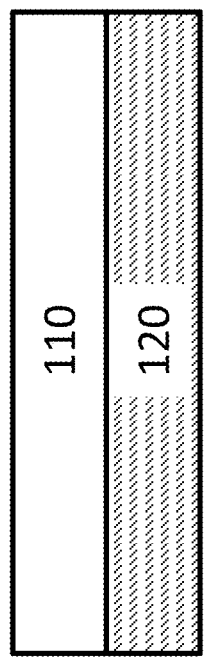
FIG. 2A schematically shows a cross-sectional view of the radiation detector.

FIG. 2A schematically shows a cross-sectional view of the radiation detector 100, according to an embodiment. The radiation detector 100 may include a radiation absorption layer 110 and an electronics layer 120 (e.g., an ASIC) for processing or analyzing electrical signals incident radiation generates in the radiation absorption layer 110. The detector 100 may or may not include a scintillator. The radiation absorption layer 110 may include a semiconductor material such as, silicon, germanium, GaAs, CdTe, CdZnTe, or a combination thereof. The semiconductor may have a high mass attenuation coefficient for the radiation of interest.

Figure 2B:
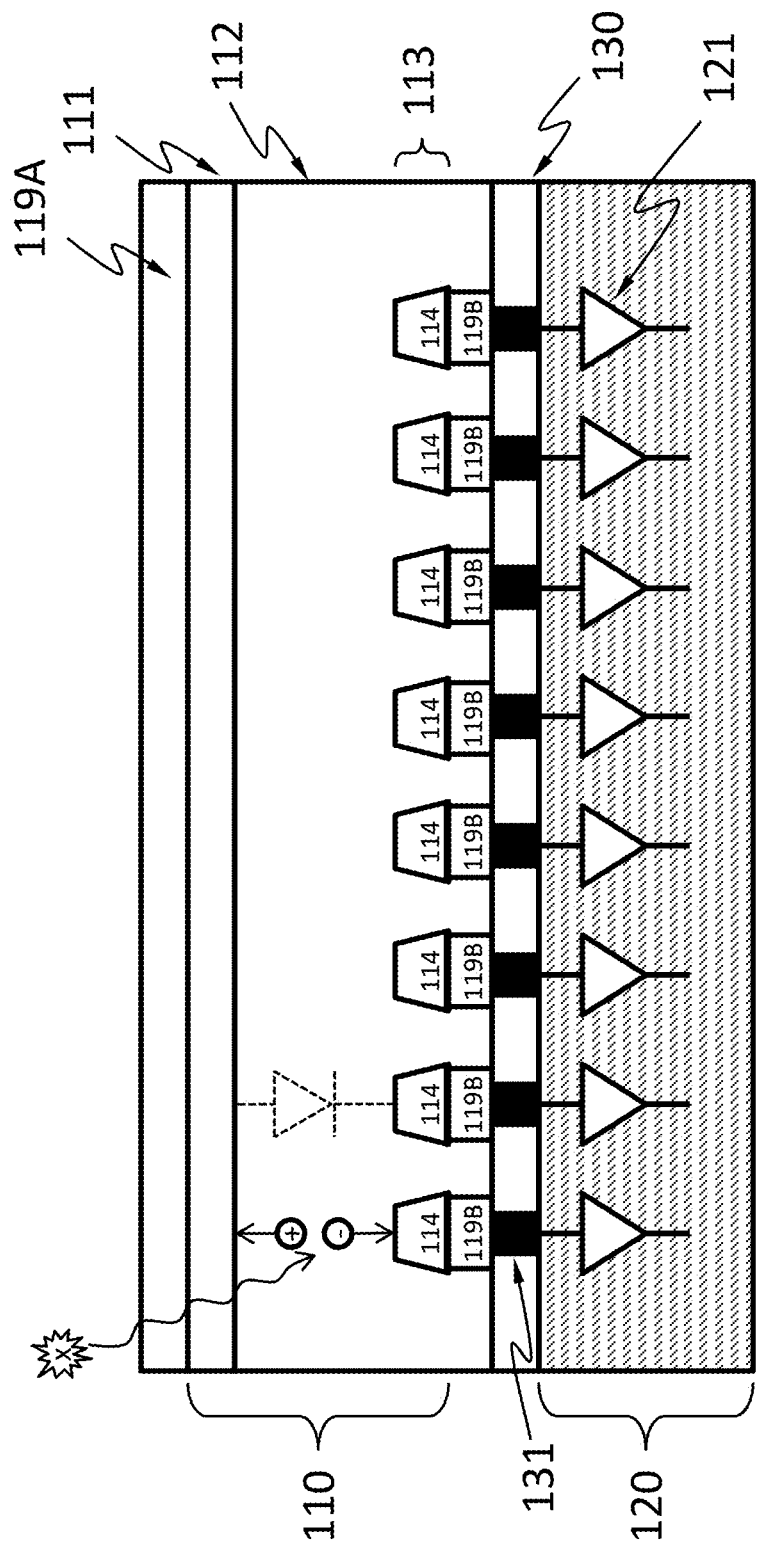
FIG. 2B schematically shows a detailed cross-sectional view of the radiation detector.

As shown in a detailed cross-sectional view of the radiation detector 100 in FIG. 2B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes having the first doped region 111 as a shared electrode. The first doped region 111 may also have discrete portions.

When radiation from the radiation source hits the radiation absorption layer 110 including diodes, the radiation photon may be absorbed and generate one or more charge carriers by a number of mechanisms. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel.

Figure 2C:
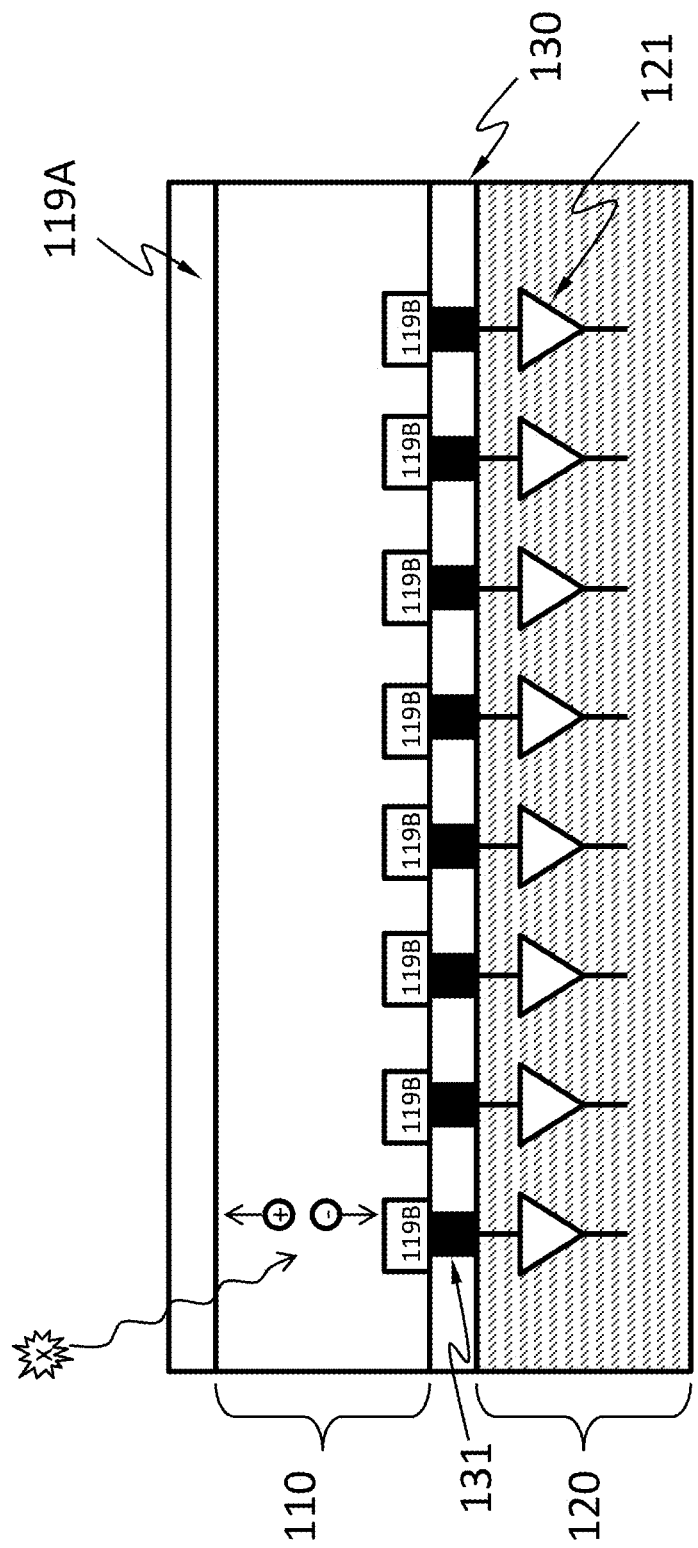
FIG. 2C schematically shows an alternative detailed cross-sectional view of the radiation detector.

As shown in an alternative detailed cross-sectional view of the radiation detector 100 in FIG. 2C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation of interest.

When the radiation hits the radiation absorption layer 110 including a resistor but not diodes, it may be absorbed and generate one or more charge carriers by a number of mechanisms. A particle of the radiation may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessors, and memory. The electronic system 121 may include one or more ADCs. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

The signals generated by the radiation incident on the radiation absorption layer 110 may be in a form of an electrical current. Likewise, the dark noise may also be in a form of an electrical current (e.g., a DC current flowing from the electric contacts 119B). If the current may be ascertained, the electrical current may be compensated for (e.g., diverted from) the electronic system 121.

Figure 3A:
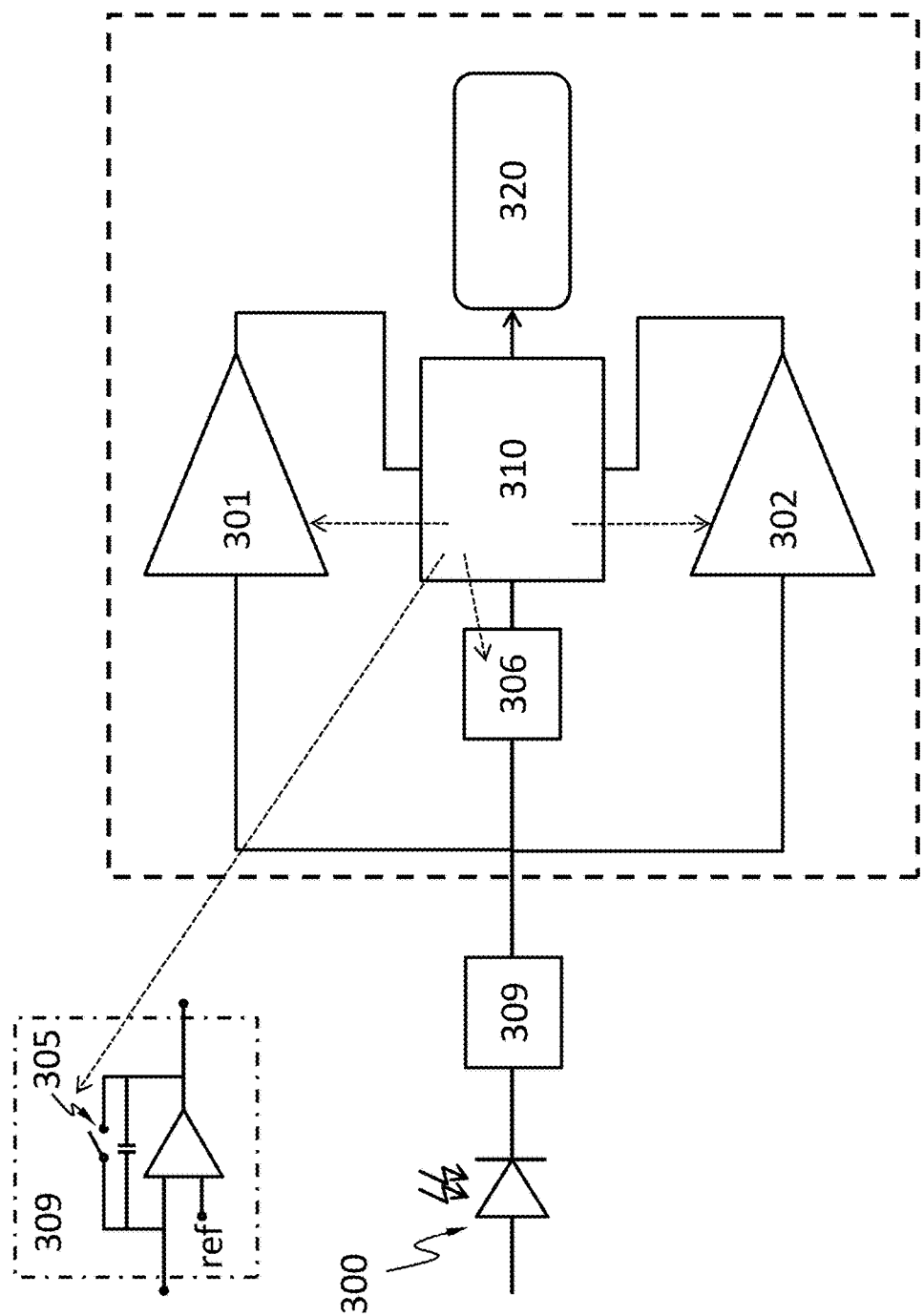
FIG. 3A and FIG. 3B each show a component diagram of an electronic system of the detector in FIG. 2B or FIG. 2C, according to an embodiment.
Figure 3B:
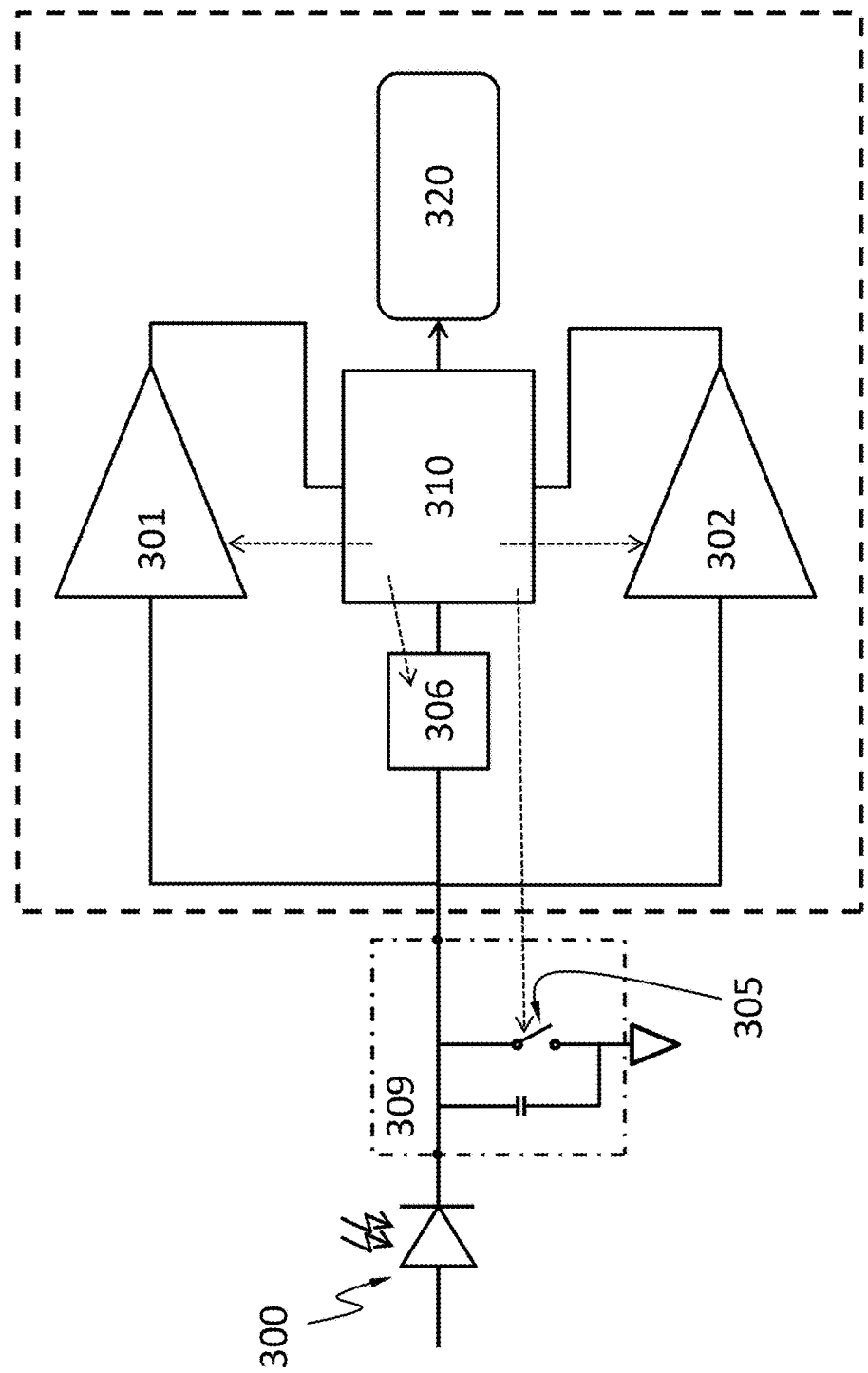

FIG. 3A and FIG. 3B each show a component diagram of the electronic system 121, according to an embodiment. The system 121 includes a capacitor module 309 electrically connected to an electrode of a diode 300 or an electrical contact, wherein the capacitor module is configured to collect charge carriers from the electrode. The capacitor module can include a capacitor and charge carriers from the electrode accumulate on the capacitor over a period of time ("integration period"). After the integration period has expired, the capacitor voltage is sampled and then reset by a reset switch. The capacitor module can include a capacitor directly connected to the electrode. The capacitor may be in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path.

The dark noise in the form of an electrical current, if not compensated for, charges the capacitor in the capacitor module 309 along with the signals generated by the radiation.

Figure 4A:
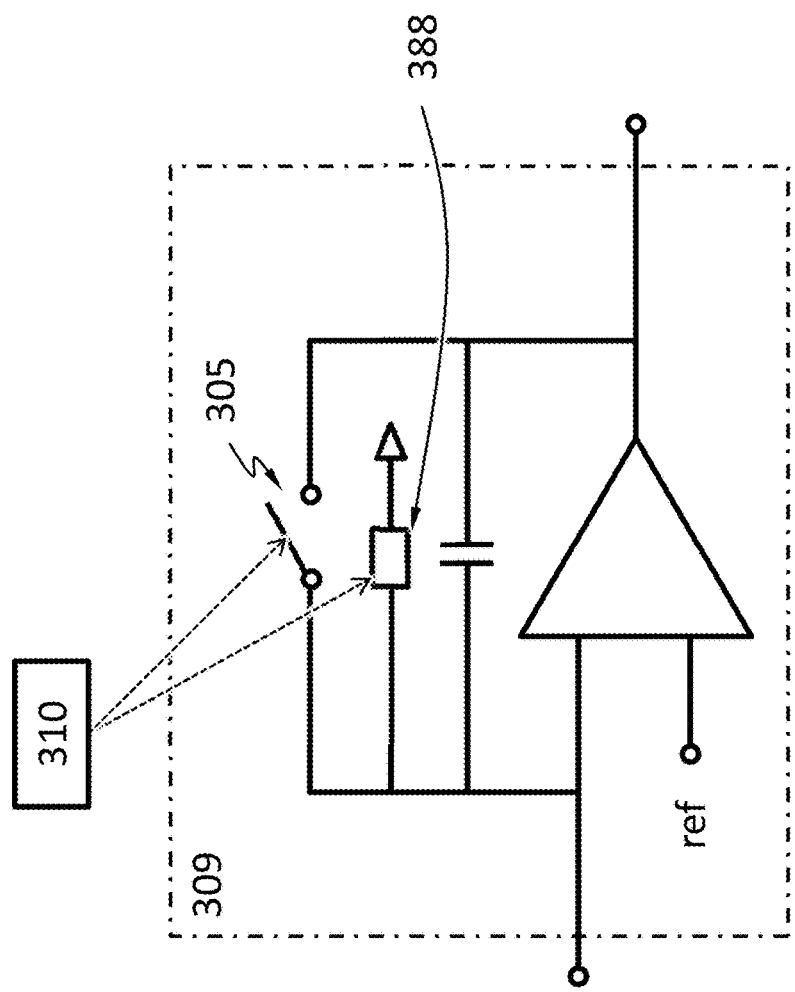

FIG. 4A and FIG. 4B respectively show a circuit configured to compensate for the dark noise in the form of an electrical current. A current sourcing module 388 is in parallel to the capacitor. The current sourcing module 388 may be adjustable such that the electrical current it sources compensates for the electrical current of the dark noise. In the circuit shown in FIG. 4A and FIG. 4B, the electrical current of the dark noise is diverted through the current sourcing module 388 so that the electrical current of the dark noise does not charge the capacitor.

Figure 5:
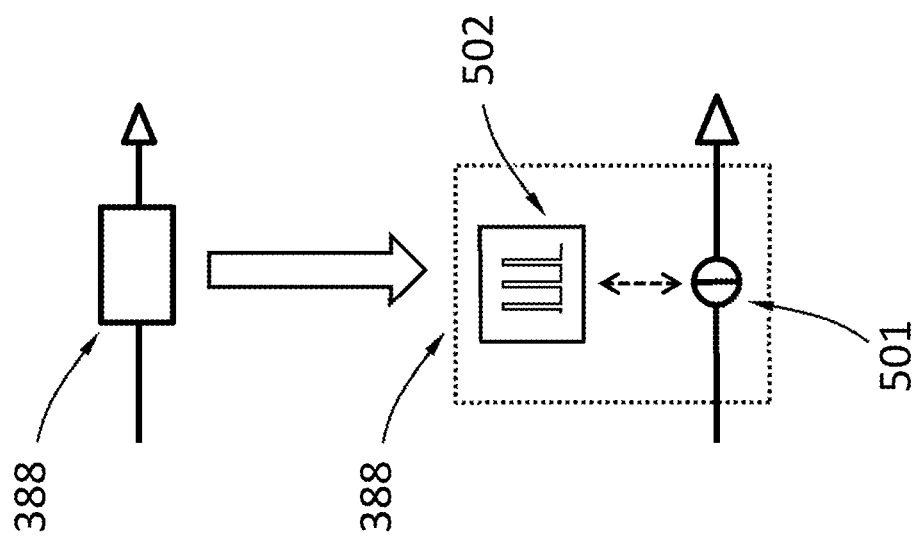
FIG. 5 schematically shows the current sourcing module in the electronic system of the radiation detector, according to an embodiment.

The electrical current of the dark noise may be a very small current, such as in the range of picoamps (e.g., 1-1000 pA). Compensating for a small electrical current may be challenging. FIG. 5 schematically shows the current sourcing module 388, according to an embodiment. The current sourcing module 388 may include a current source 501 and a modulator 502. The current source 501 is configured to output a first electrical current and a second electrical current. The first electrical current and the second electrical current are different in their magnitude, direction, or both. The modulator 502 controls the ratio of the duration at which the current source 501 outputs the first electrical current to the duration at which the current source 501 outputs the second electrical current. The first electrical current and the second electrical current may not be as small as the electrical current of the dark noise but the temporal average of the electrical current the current sourcing module 388 sources, as a result of the modulation by the modulator 502, may be equal to the electrical current of the dark noise. For example, at least one of the first electrical current and the second electrical current is at least an order of magnitude larger than the electrical current of the dark noise. For example, if the first electrical current is 1 nA and the second electrical current is 0, and the ratio is 1:999, the temporal average of the electrical current the current sourcing module 388 sources is 1 pA. The modulator 502 may be as simple as a switch. The modulator 502 may have complex circuitry such as a processor or a memory.

Figure 7:
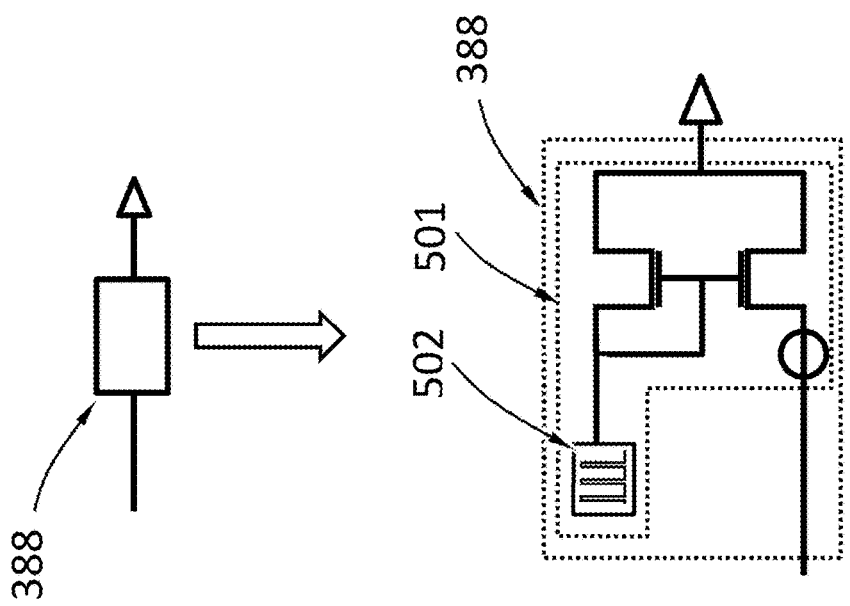
FIG. 6 and FIG. 7 show two examples of the current sourcing module, where the current source of the current sourcing module includes a current mirror.
Figure 6:
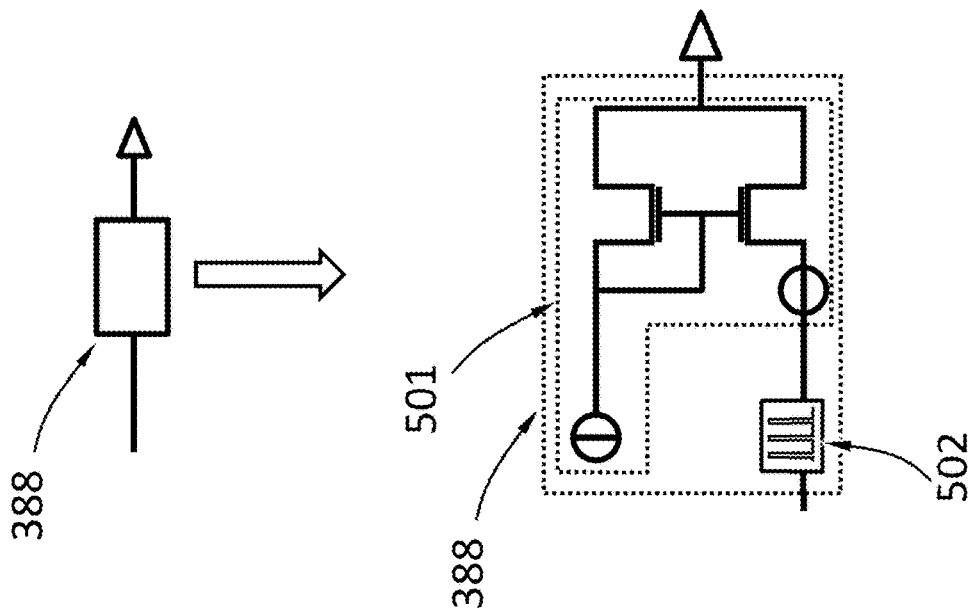

FIG. 6 and FIG. 7 show two examples of the current sourcing module 388, where the current source 501 includes a current mirror. A current mirror is a circuit that receives an input electrical current and outputs an output electrical current proportional to the input electrical current. A current mirror can be viewed as a current-controlled current source (CCCS). A current mirror may include two cascaded current-to-voltage and voltage-to-current converters placed at the same conditions and having reverse characteristics. A current mirror may be implemented using MOSFET transistors as shown here. A current mirror may be implemented using bipolar junction transistors. The modulator 502 may be located on the output stage of the current mirror, as shown in FIG. 6. For example, the modulator 502 may include a switch that controllably connects the current sourcing module 388 to and disconnects it from the capacitor in the capacitor module 309. The modulator 502 may be located on the input stage of the current mirror, as shown in FIG. 7. The modulator 502 may include a current source outputting electrical current at alternating magnitudes. The modulator 502 may include a current source outputting two magnitudes of electrical current with adjustable ratio of durations.

Figure 8:
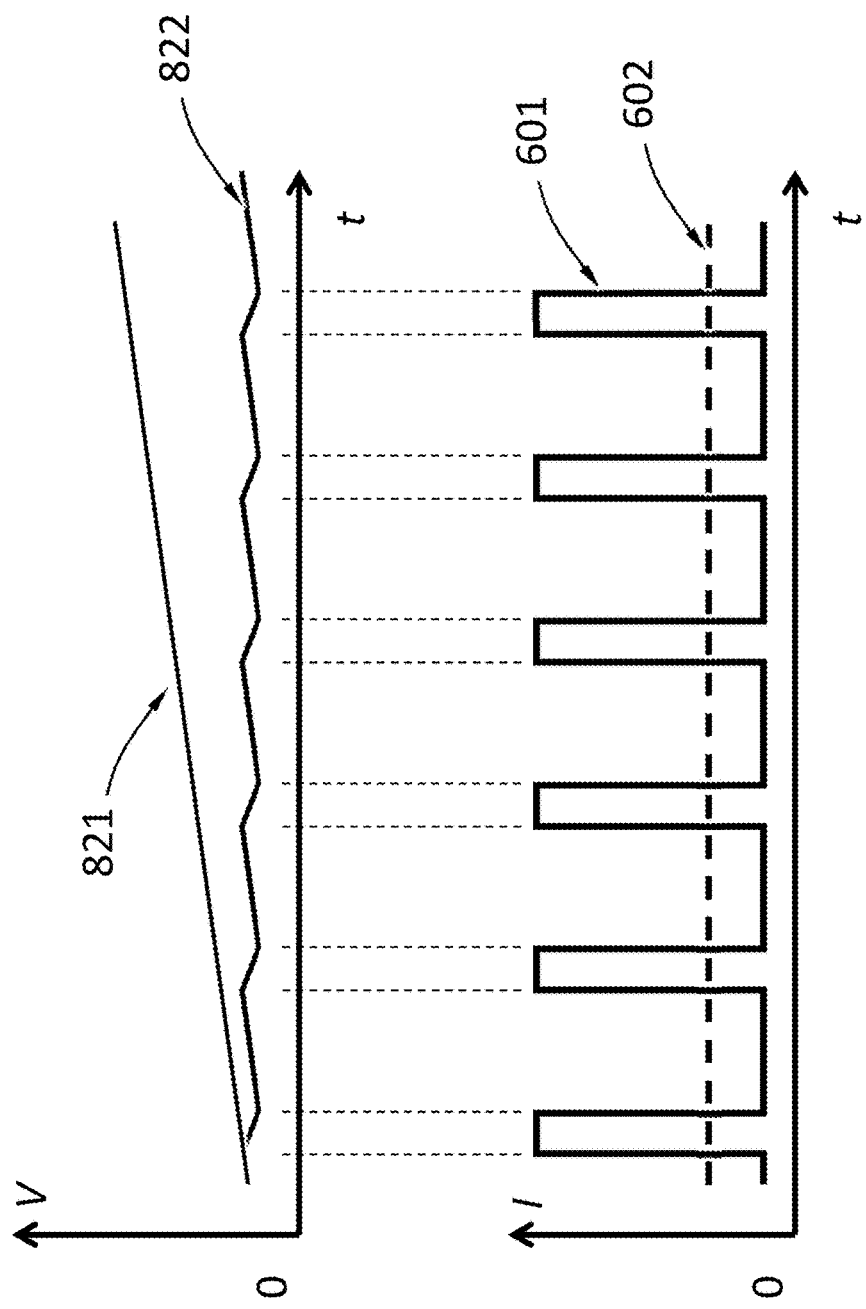
FIG. 8 schematically shows the electrical current the current sourcing module sources, the voltage across the capacitor of the capacitor module attributable to the dark noise and the electrical current the current sourcing module provides, the voltage across the capacitor of the capacitor module attributable to only the dark noise, as functions of time.

FIG. 8 schematically shows the electrical current 601 the current sourcing module 388 sources, as a function of time. The dotted line 602 shows the temporal average of the electrical current 601. FIG. 8 also schematically shows the voltage 822 across the capacitor of the capacitor module 309 attributable to the dark noise and the electrical current the current sourcing module 388 provides, as a function of time. FIG. 8 also schematically shows the voltage 821 across the capacitor of the capacitor module 309 attributable to only the dark noise, as a function of time. It can be observed from FIG. 8 that the electrical current the current sourcing module 388 provides, on temporal average, removes the effect of the dark noise on the voltage across the capacitor.

Figure 9:
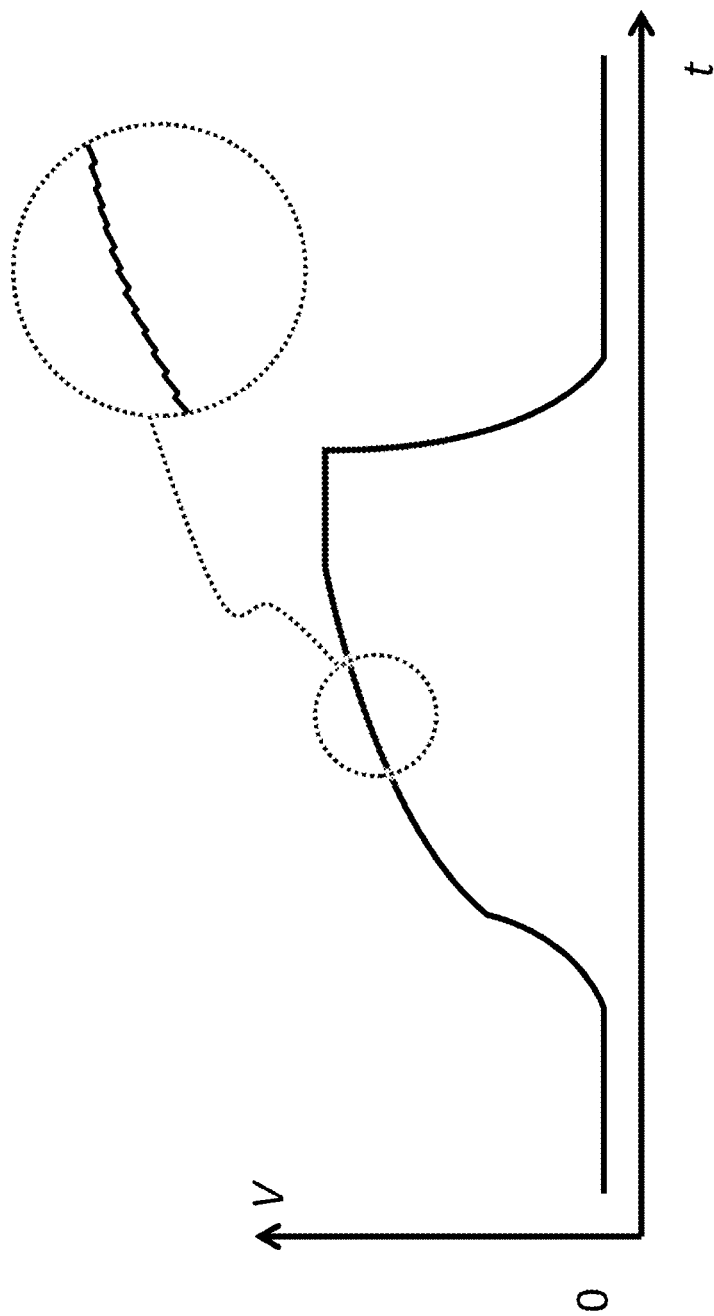
FIG. 9 schematically shows a voltage across the capacitor as a function of time, where the capacitor module includes the current sourcing module.

FIG. 9 schematically shows a voltage across the capacitor as a function of time, where the capacitor module 309 includes the current sourcing module 388. A fine saw tooth waveform superimposed on a smoothly changing voltage can be seen in FIG. 9. The saw tooth waveform is attributable to the dark noise and the electrical current the current sourcing module 388 provides, as a function of time.

Figure 10:
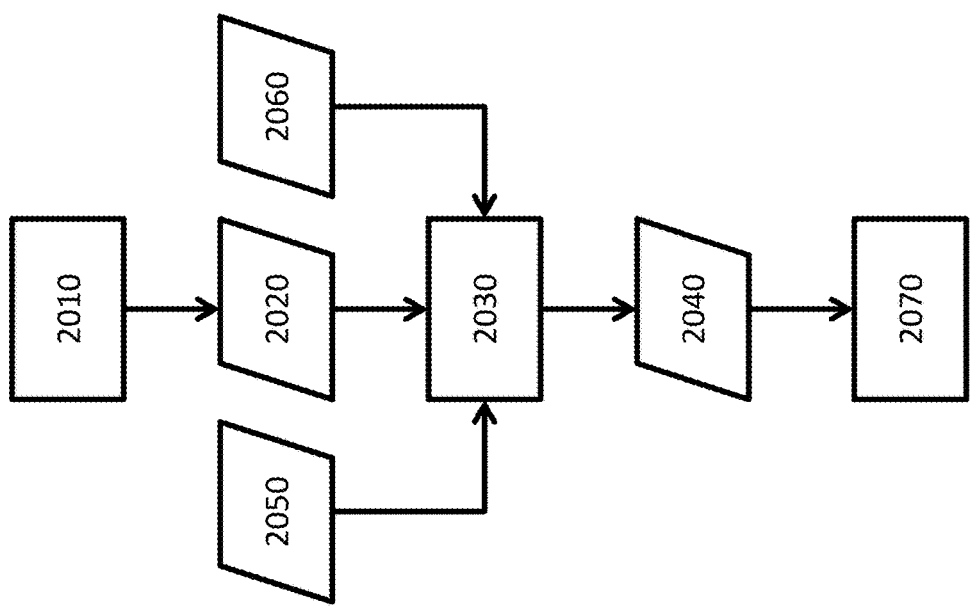
FIG. 10 schematically shows a flow chart for a method of compensating for dark noise in a radiation detector.

FIG. 10 schematically shows a flow chart for a method of compensating for dark noise in a radiation detector. In procedure 2010, a contribution 2020 of a dark noise in the signals of the radiation detector is determined. For example, the contribution may be determined by measuring the signals while the radiation detector receives no radiation. In procedure 2030, a ratio 2040 of a duration of a first compensatory signal 2050 to a duration of a second compensatory signal 2060 is determined based on the contribution 2020 of the dark noise, the first compensatory signal 2050 and the second compensatory signal 2060. For example, the first compensatory signal 2050 and the second compensatory signal 2060 may be the first electrical current and the second electrical current output by the current source 501. In procedure 2070, the signals of the radiation detector are compensated for the dark noise with the first compensatory signal 2050 and the second compensatory signal 2060 with their respective durations with the ratio 2040.

Figure 11A:
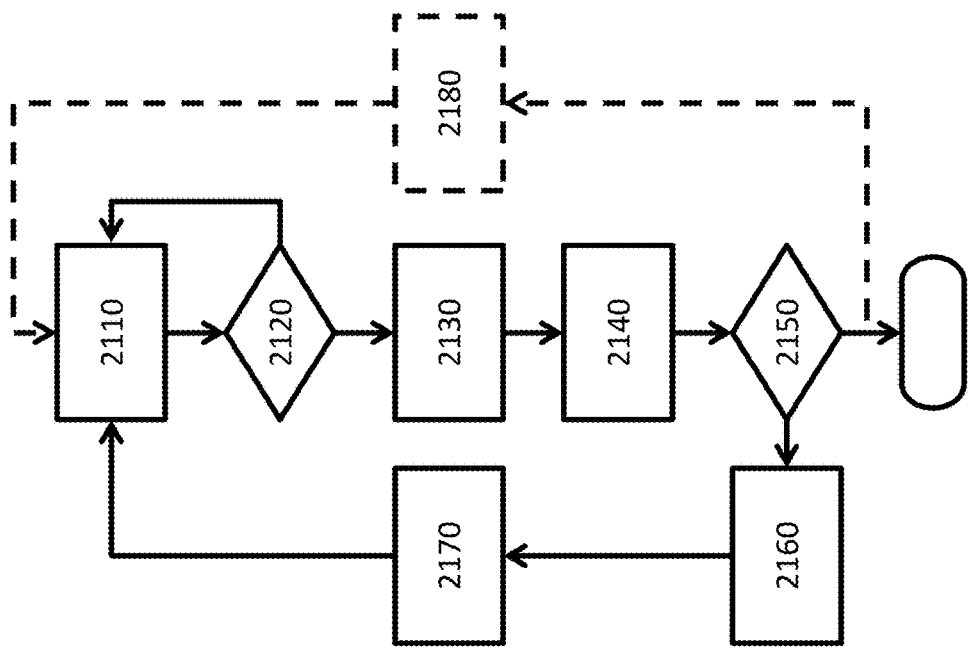
FIG. 11A schematically shows a flow chart for a method of compensating for dark noise in a radiation detector.

FIG. 11A schematically shows a flow chart for a method of compensating for dark noise in a radiation detector. In procedure 2110, signals of the radiation detector are measured, when the radiation detector receives no radiation and a compensation for the dark noise of the radiation detector is present. In procedure 2120, if the signals have not exceeded a first level, the flow goes back the procedure 2110; if the signals have exceeded the first level, a time delay is commenced in procedure 2130. In procedure 2140, the signals of the radiation detector at the end of the time delay are measured. In procedure 2150, if the signals do not exceed a second level, the flow ends and the current magnitude of compensation is deemed sufficient to compensate for the contribution of the dark noise; if the signals at the end of the time delay exceed the second level, the compensation for the dark noise is increased in procedure 2160, the signals are reset in procedure 2170, and the flow goes back the procedure 2110. Alternatively, in procedure 2150, if the signals do not exceed a second level, the second level is lowered in procedure 2180 and the flow goes back the procedure 2110; if the signals at the end of the time delay exceed the second level, the compensation for the dark noise is increased in procedure 2160, the signals are reset in procedure 2170, and the flow goes back the procedure 2110. When the compensation for the dark noise is increased, it may be increased to a magnitude among a group of discrete values. The current magnitude of compensation may be stored in a memory in the radiation detector.

FIG. 11B schematically shows a flow chart for a method of compensating for dark noise in a radiation detector. In procedure 2210, signals of the radiation detector are measured, when the radiation detector receives no radiation and a compensation for the dark noise of the radiation detector is present. In procedure 2220, if the signals have not exceeded a first level, the flow goes back the procedure 2210; if the signals have exceeded the first level, a time delay is commenced in procedure 2230. In procedure 2240, the signals of the radiation detector at the end of the time delay are measured. In procedure 2250, the difference of the signals at the beginning of the time delay (which may simply be the first level) and the signals at the end of the time delay is determined. In procedure 2260, the magnitude of the compensation for the dark noise is determined based on the difference.

In addition the capacitor module 309, which includes the current sourcing module 388, the electronic system 121 may further include a first voltage comparator 301, a second voltage comparator 302, a counter 320, a switch 305, a voltmeter 306 and a controller 310, as shown in FIG. 3A and FIG. 3B.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

The controller 310 may be configured to control the current sourcing module 388. For example, the controller 310 may change the magnitude of compensation for the dark noise by controlling the current sourcing module 388. The controller 310 may adjust the ratio 2040 of the duration of the first compensatory signal 2050 to the duration of a second compensatory signal 2060 ratio in the flow of FIG. 10. The controller 310 may execute instructions and thereby implement the flows of FIG. 10 and FIG. 11.

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 12:
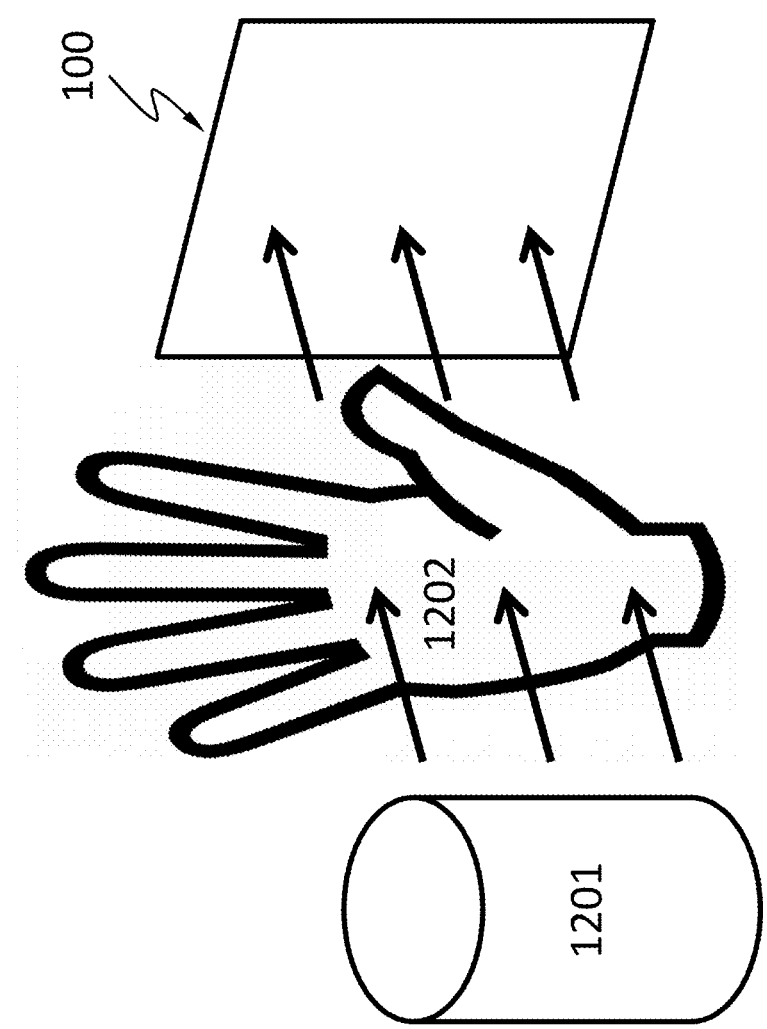
FIG. 12-FIG. 18 each schematically show a system comprising the radiation detector described herein.

FIG. 12 schematically shows a system comprising the radiation detector 100 described herein. The system may be used for medical imaging such as chest X-ray radiography, abdominal X-ray radiography, etc. The system comprises a pulsed radiation source 1201 that emits X-ray. X-ray emitted from the pulsed radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the radiation detector 100. The radiation detector 100 forms an image by detecting the intensity distribution of the X-ray.

Figure 13:
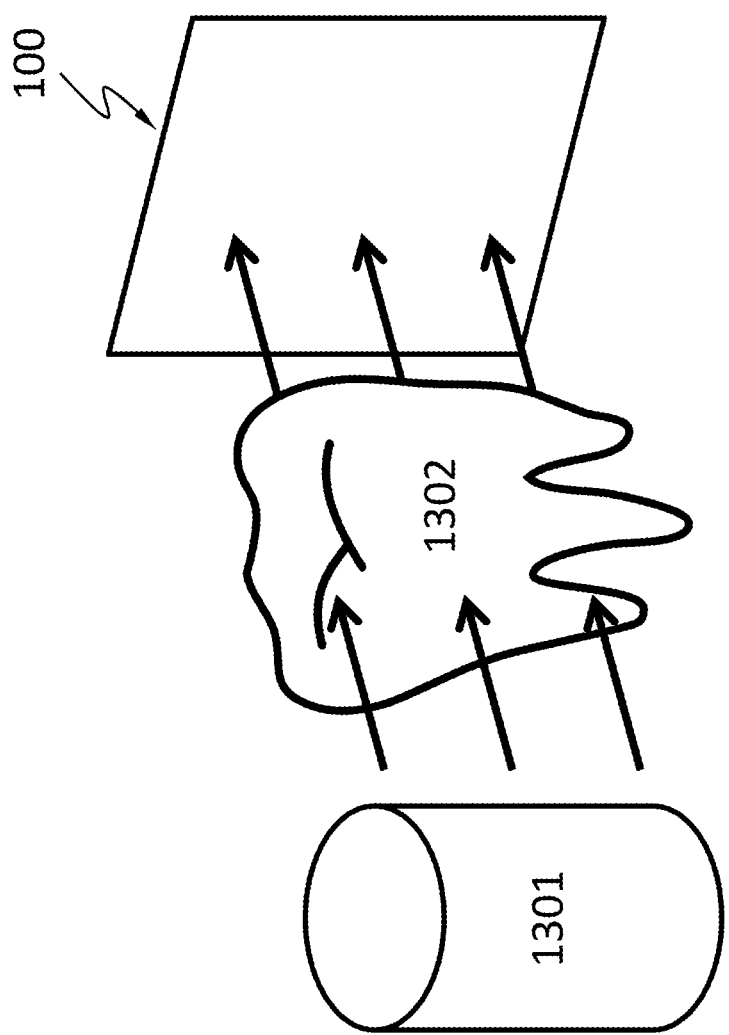

FIG. 13 schematically shows a system comprising the radiation detector 100 described herein. The system may be used for medical imaging such as dental X-ray radiography. The system comprises a pulsed radiation source 1301 that emits X-ray. X-ray emitted from the pulsed radiation source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the radiation detector 100. The radiation detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 14:
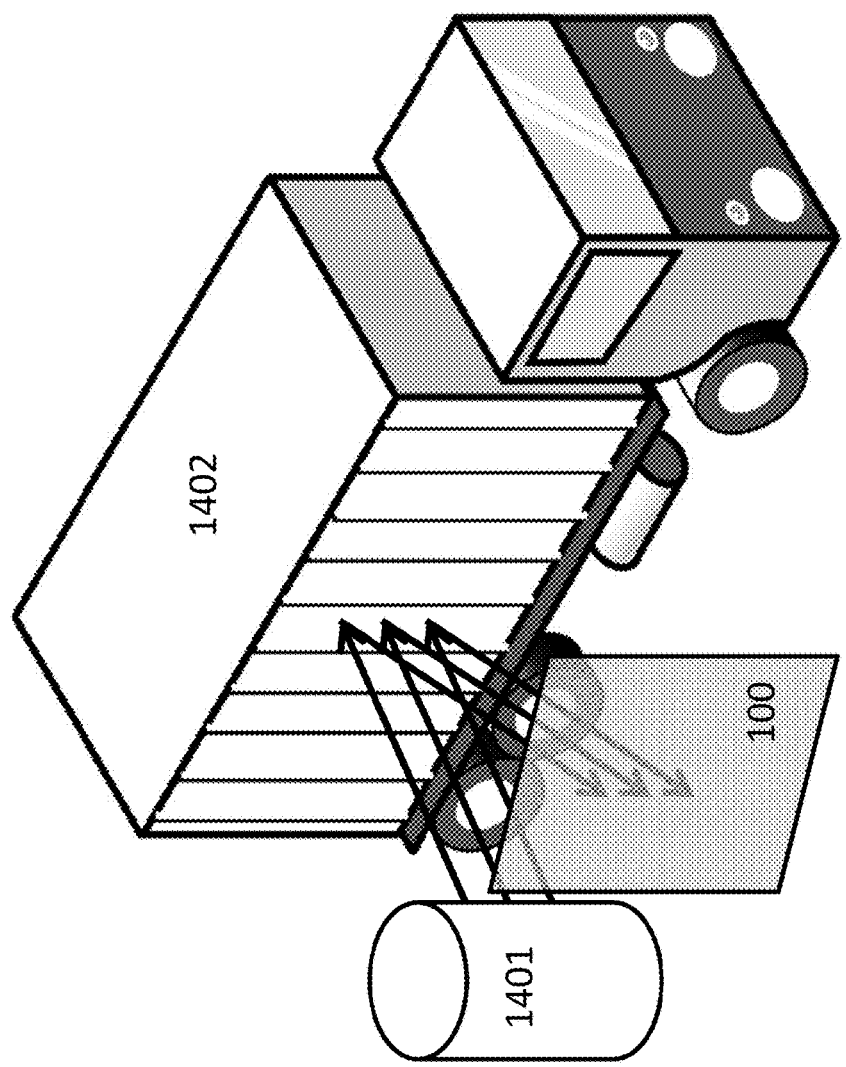

FIG. 14 schematically shows a cargo scanning or non-intrusive inspection (NII) system comprising the radiation detector 100 described herein. The system may be used for inspecting and identifying goods in transportation systems such as shipping containers, vehicles, ships, luggage, etc. The system comprises a pulsed radiation source 1401. Radiation emitted from the pulsed radiation source 1401 may backscatter from an object 1402 (e.g., shipping containers, vehicles, ships, etc.) and be projected to the radiation detector 100. Different internal structures of the object 1402 may backscatter the radiation differently. The radiation detector 100 forms an image by detecting the intensity distribution of the backscattered radiation and/or energies of the backscattered radiation.

Figure 15:
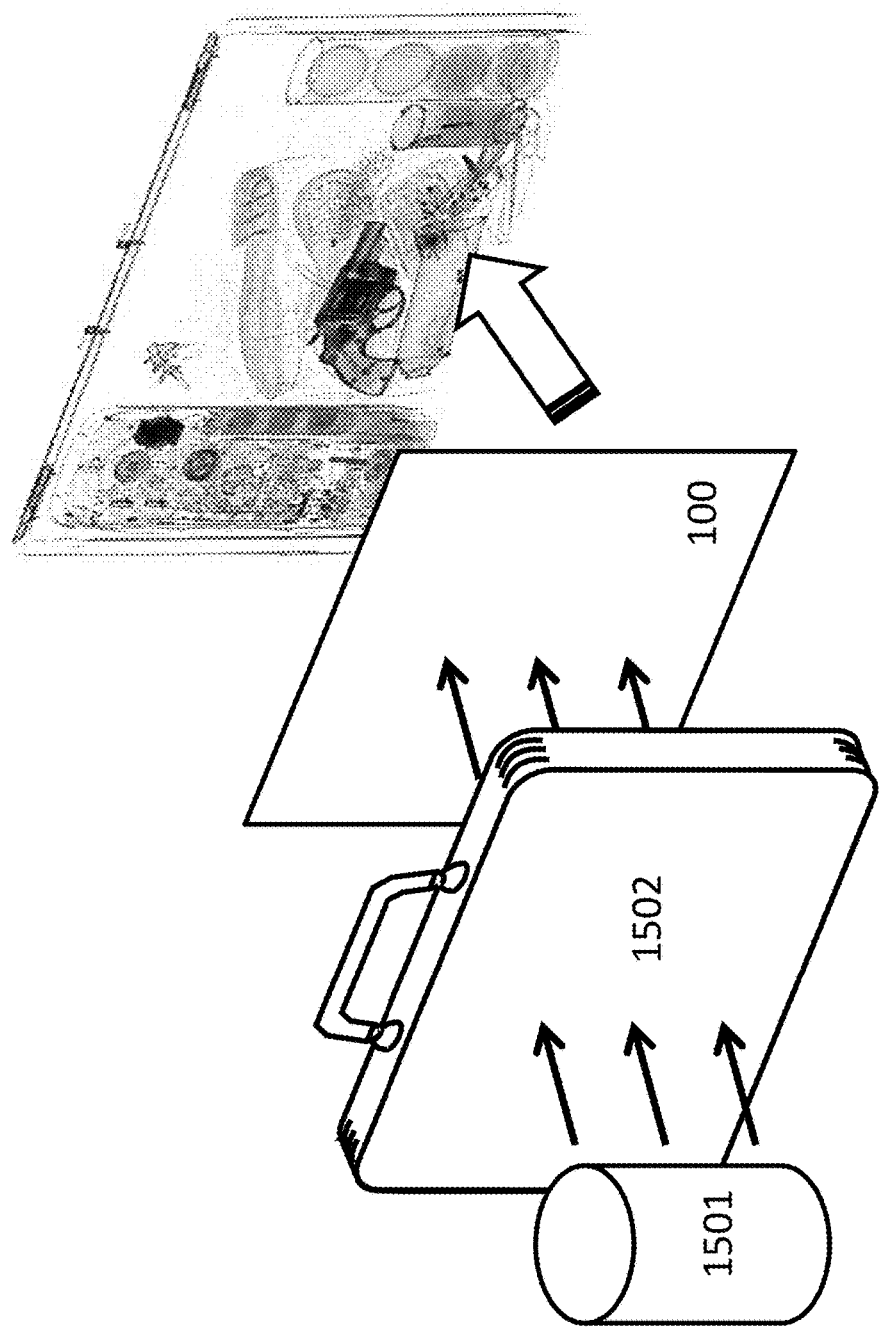

FIG. 15 schematically shows another cargo scanning or non-intrusive inspection (NII) system comprising the radiation detector 100 described herein. The system may be used for luggage screening at public transportation stations and airports. The system comprises a pulsed radiation source 1501 that emits X-ray. X-ray emitted from the pulsed radiation source 1501 may penetrate a piece of luggage 1502, be differently attenuated by the contents of the luggage, and projected to the radiation detector 100. The radiation detector 100 forms an image by detecting the intensity distribution of the transmitted X-ray. The system may reveal contents of luggage and identify items forbidden on public transportation, such as firearms, narcotics, edged weapons, flammables.

Figure 16:
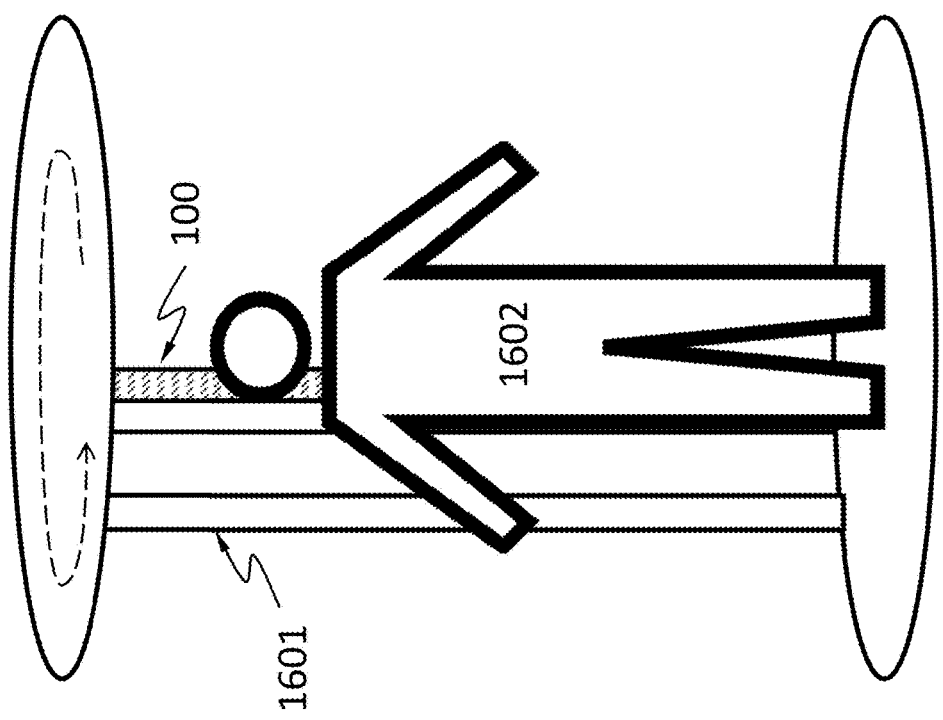

FIG. 16 schematically shows a full-body scanner system comprising the radiation detector 100 described herein. The full-body scanner system may detect objects on a person's body for security screening purposes, without physically removing clothes or making physical contact. The full-body scanner system may be able to detect non-metal objects. The full-body scanner system comprises a pulsed radiation source 1601. The radiation emitted from the pulsed radiation source 1601 may backscatter from a human 1602 being screened and objects thereon, and be projected to the radiation detector 100. The objects and the human body may backscatter the radiation differently. The radiation detector 100 forms an image by detecting the intensity distribution of the backscattered radiation. The radiation detector 100 and the pulsed radiation source 1601 may be configured to scan the human in a linear or rotational direction.

Figure 17:
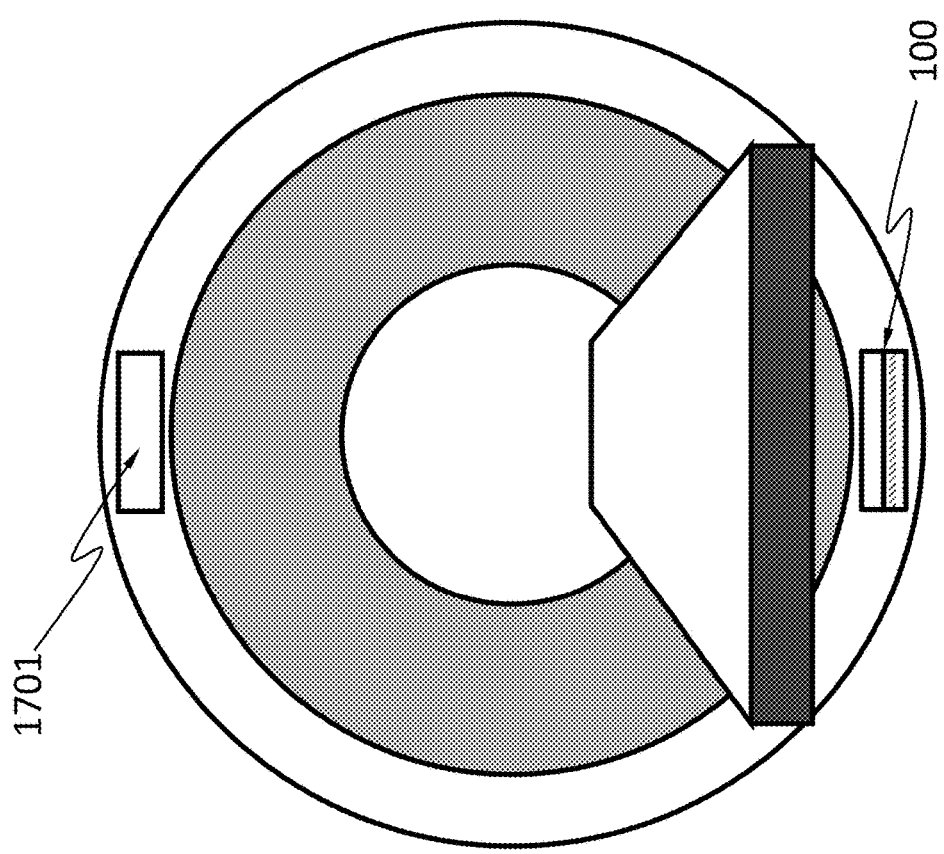

FIG. 17 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the radiation detector 100 described herein and a pulsed radiation source 1701 that emits X-ray. The radiation detector 100 and the pulsed radiation source 1701 may be configured to rotate synchronously along one or more circular or spiral paths.

Figure 18:
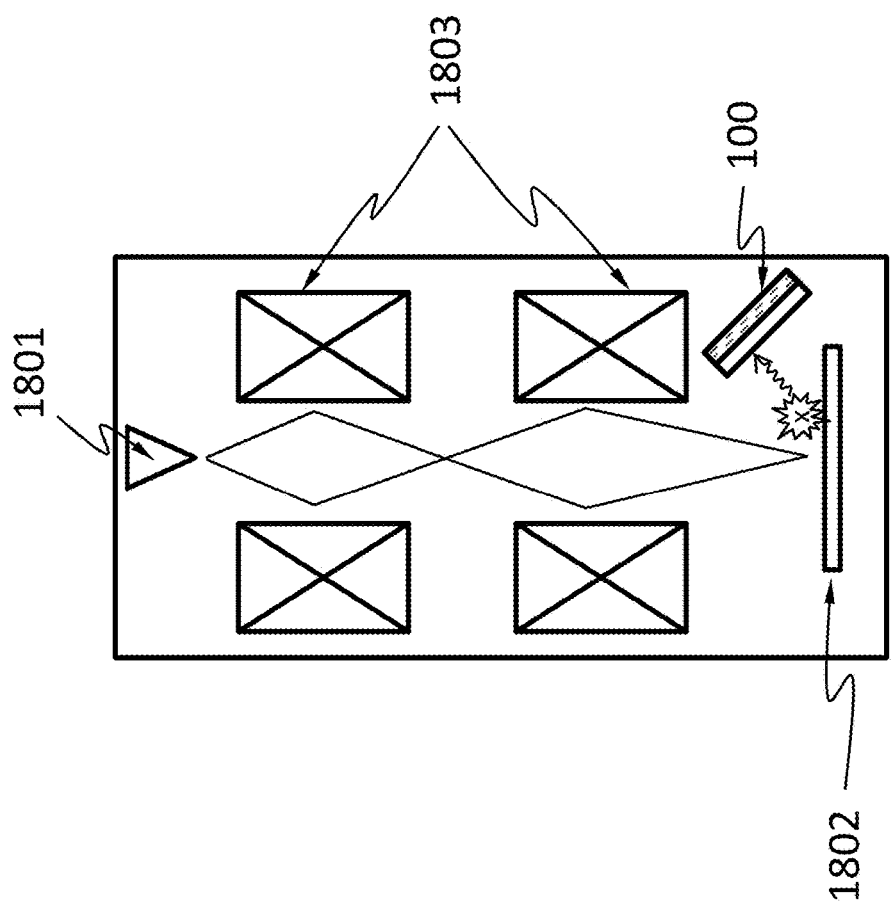

FIG. 18 schematically shows an electron microscope. The electron microscope comprises an electron source 1801 (also called an electron gun) that is configured to emit electrons.

The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the radiation detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the radiation detector 100.

The radiation detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or an X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A radiation detector, comprising:
   a radiation absorption layer comprising an electrode;
   a capacitor module electrically connected to the electrode and comprising a capacitor, wherein the capacitor module is configured to collect charge carriers from the electrode onto the capacitor;
   a current sourcing module in parallel to the capacitor, the current sourcing module configured to compensate for an electrical current of a dark noise in the radiation detector and comprising a current source and a modulator;
   wherein the current source is configured to output a first electrical current and a second electrical current;
   wherein the modulator is configured to control a ratio of a duration at which the current source outputs the first electrical current to a duration at which the current source outputs the second electrical current.

2. The radiation detector of claim 1, wherein the current sourcing module is adjustable.

3. The radiation detector of claim 1, wherein the current sourcing module is configured to divert the electrical current of the dark noise through the current sourcing module.

4. The radiation detector of claim 1, wherein the first electrical current and the second electrical current are different in their magnitude, direction, or both.

5. The radiation detector of claim 1, wherein at least one of the first electrical current and the second electrical current is at least an order of magnitude larger than the electrical current of the dark noise.

6. The radiation detector of claim 1, wherein the electrical current of the dark noise is from 1 pA to 1000 pA.

7. The radiation detector of claim 1, wherein the modulator comprises a processor or a memory.

8. The radiation detector of claim 1, wherein the modulator comprises a switch.

9. The radiation detector of claim 1, wherein the radiation is X-ray.

10. The radiation detector of claim 1, wherein the current source comprises a current mirror.

11. The radiation detector of claim 10, wherein the modulator is located on an input stage of the current mirror.

12. The radiation detector of claim 11, wherein the modulator comprises a current source configured to output electrical current at alternating magnitudes.

13. The radiation detector of claim 11, wherein the modulator comprises a current source configured to output two magnitudes of electrical current with adjustable ratio of durations.

14. The radiation detector of claim 10, wherein the modulator is located on an output stage of the current mirror.

15. The radiation detector of claim 14, wherein the modulator comprises a switch configured to controllably connect the current sourcing module to and to controllably disconnect it from the capacitor.

16. The radiation detector of claim 1, further comprising:
   a first voltage comparator configured to compare a voltage of the electrode to a first threshold;
   a second voltage comparator configured to compare the voltage to a second threshold;
   a counter configured to register a number of X-ray photons absorbed by the X-ray absorption layer;
   a controller;
   wherein the controller is configured to start a time delay from a time at which the first voltage comparator determines that an absolute value of the voltage equals or exceeds an absolute value of the first threshold;
   wherein the controller is configured to activate the second voltage comparator during the time delay;
   wherein the controller is configured to cause the number registered by the counter to increase by one, if the second voltage comparator determines that an absolute value of the voltage equals or exceeds an absolute value of the second threshold.

17. The radiation detector of claim 16, wherein the controller is configured to activate the second voltage comparator at a beginning or expiration of the time delay.

18. The radiation detector of claim 16, further comprising a voltmeter, wherein the controller is configured to cause the voltmeter to measure the voltage upon expiration of the time delay.

19. The radiation detector of claim 18, wherein the controller is configured to determine a photon energy based on a value of the voltage measured upon expiration of the time delay.

20. The radiation detector of claim 16, wherein the controller is configured to connect the electrode to an electrical ground.

21. The radiation detector of claim 16, wherein a rate of change of the voltage is substantially zero at expiration of the time delay.

22. The radiation detector of claim 16, wherein a rate of change of the voltage is substantially non-zero at expiration of the time delay.

23. The radiation detector of claim 1, wherein the radiation absorption layer comprises a diode.

24. The radiation detector of claim 1, wherein the radiation absorption layer comprises silicon, germanium, GaAs, CdTe, CdZnTe, or a combination thereof.

25. The radiation detector of claim 1, wherein the radiation detector does not comprise a scintillator.

26. The radiation detector of claim 1, wherein the radiation detector comprises an array of pixels.

27. A system comprising the radiation detector of claim 1 and an X-ray source, wherein the system is configured to perform X-ray radiography on human chest or abdomen.

28. A system comprising the radiation detector of claim 1 and an X-ray source, wherein the system is configured to perform X-ray radiography on human mouth.

29. A cargo scanning or non-intrusive inspection (NII) system, comprising the radiation detector of claim 1 and an X-ray source, wherein the cargo scanning or non-intrusive inspection (NII) system is configured to form an image using backscattered X-ray.

30. A cargo scanning or non-intrusive inspection (NII) system, comprising the radiation detector of claim 1 and an X-ray source, wherein the cargo scanning or non-intrusive inspection (NII) system is configured to form an image using X-ray transmitted through an object inspected.

31. A full-body scanner system comprising the radiation detector of claim 1 and a radiation source.

32. A computed tomography (CT) system comprising the radiation detector of claim 1 and a radiation source.

33. An electron microscope comprising the radiation detector of claim 1, an electron source and an electronic optical system.

34. A system comprising the radiation detector of claim 1, wherein the system is an X-ray telescope, or an X-ray microscopy, or wherein the system is configured to perform mammography, industrial defect detection, microradiography, casting inspection, weld inspection, or digital subtraction angiography.

35. A method comprising:
determining a contribution of a dark noise in signals of a radiation detector;
determining a ratio of a duration of a first compensatory signal to a duration of a second compensatory signal based on the contribution of the dark noise, the first compensatory signal and the second compensatory signal; and
compensating the signals of the radiation detector for the dark noise with the first compensatory signal and the second compensatory signal with their respective durations with the ratio.

36. The method of claim 35, wherein the contribution is determined by measuring the signals while the radiation detector receives no radiation.

37. The method of claim 35, wherein the first compensatory signal and the second compensatory signal are electrical currents.

38. A method comprising:
measuring signals of a radiation detector when the radiation detector receives no radiation and a compensation for the dark noise of the radiation detector is present;
if the signals have exceeded a first level, commencing a time delay;
measuring the signals of the radiation detector at an end of the time delay; and
if the signals at the end of the time delay exceed a second level, increasing the compensation for the dark noise.

39. The method of claim 38, wherein the compensation is increased to a magnitude among a group of discrete values.

40. The method of claim 38, further comprising:
if the signals at the end of the time delay exceed a second level, resetting the signals.

41. A method comprising:
measuring signals of a radiation detector when the radiation detector receives no radiation and a compensation for the dark noise of the radiation detector is present;
if the signals have exceeded a first level, commencing a time delay;
measuring the signals of the radiation detector at an end of the time delay;
determining a difference between the signals at the end of the time delay and the signals at the beginning of the time delay; and
determining a magnitude of the compensation based on the difference.

* * * * *